US00PP36020P2

(12) United States Plant Patent
Kerley et al.

(10) Patent No.: US PP36,020 P2
(45) Date of Patent: Jul. 16, 2024

(54) ***PRIMULA* PLANT NAMED 'KERBELRIP'**

(50) Latin Name: *Primula vulgaris*
Varietal Denomination: KERBELRIP

(71) Applicants: David William Kerley, Over (GB); Timothy Edward Kerley, Willingham (GB)

(72) Inventors: David William Kerley, Over (GB); Timothy Edward Kerley, Willingham (GB)

(73) Assignee: Kerley & Co., LTD. (GB)

( * ) Notice: Subject to any disclaimer, the term of this patent is extended or adjusted under 35 U.S.C. 154(b) by 0 days.

(21) Appl. No.: 18/236,006

(22) Filed: Aug. 21, 2023

(51) Int. Cl.
*A01H 6/00* (2018.01)
*A01H 5/02* (2018.01)

(52) U.S. Cl.
USPC ..... Plt./472

(58) Field of Classification Search
USPC ..... Plt./472
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Primula vulgaris* plant named 'KERBELRIP' is disclosed, characterized by abundant, blue-violet and white bi-color, double flowers. Plants are vigorous and sterile, with upright, compact habits. The new variety is a *Primula vulgaris*, suitable for outdoor landscape and container use.

2 Drawing Sheets

Figure 1:
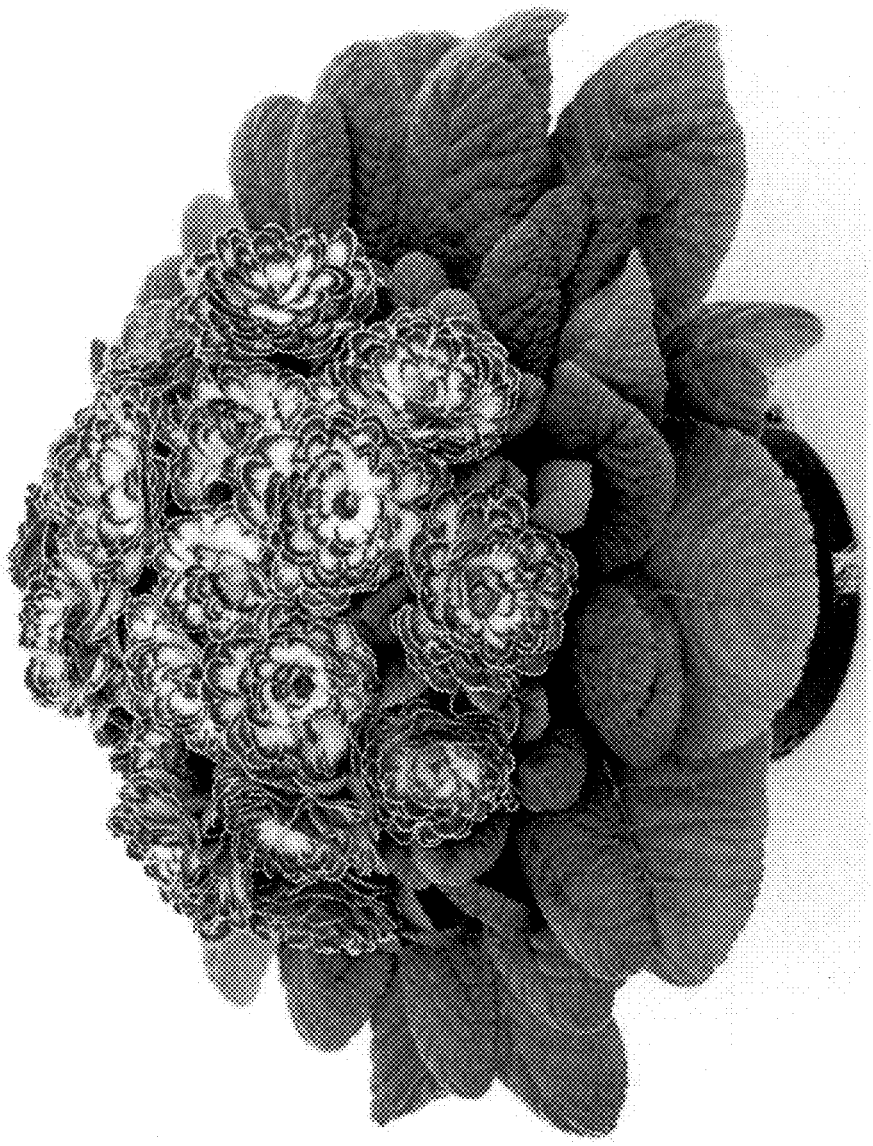

Latin name of the genus and species: *Primula vulgaris.*
Variety denomination: 'KERBELRIP'.

BACKGROUND OF THE INVENTION

The new cultivar is the product of a planned breeding program under the direction of the inventors. The objective of the breeding program was to produce new *Primula* cultivars with abundant double flowers for commercial ornamental purposes. The new cultivar resulted from crossing of the seed parent, an unpatented, unnamed, proprietary variety of *Primula*, and the pollen parent, a different unnamed, unpatented, proprietary variety of *Primula*. The crossing resulting in the new variety was made in April of 2015 at a research greenhouse in Cambridge, United Kingdom. Selection of the new variety 'Kerbelrip' was made in March of 2016, by the inventor inventors at a research greenhouse located in Cambridge, United Kingdom.

Asexual reproduction of the new cultivar 'KERBELRIP' was first performed in the United Kingdom during May of 2016, by tissue culture. This and subsequent propagation has shown that the unique features of this cultivar are stable and reproduced true to type in successive generations.

SUMMARY OF THE INVENTION

The cultivar 'KERBELRIP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBELRIP'. These characteristics in combination distinguish 'KERBELRIP' as a new and distinct *Primula* cultivar:

1. Double flowers.
2. Blue-violet and white bi-color flowers.
3. Abundant flowering.

4. Large calyx that frames the flowers.
5. Upright, compact and uniform plant habit.

PARENT COMPARISONS

Plants of the new cultivar 'KERBELRIP' are similar to plants of the seed parent, in most horticultural characteristics. However, plants of the new cultivar differ in the following ways:

1. New cultivar has double flowers; seed parent is single flowered.
2. New variety is sterile; seed parent is fertile.

Plants of the new cultivar 'KERBELRIP' are similar to plants of the pollen parent, in most horticultural characteristics. However, plants of the new cultivar differ in the following ways:

1. New cultivar has double flowers; pollen parent is single flowered.
2. New variety is sterile; pollen parent is fertile.

COMMERCIAL COMPARISONS

Plants of the new variety can be compared to plants of the *Primula* cultivar 'Kerbelil', unpatented. Plants of the new *Primula* differed from plants of the cultivar 'Kerbelil' in the following characteristics:

1. The comparator's flower rim color is purple; flower rim color of 'Kerbelrip' is blue- violet.
2. Sepals of 'Kerbelil' are smaller than sepals of 'Kerbelrip'.
3. Plants of 'Kerbelil' are more compact than plants of 'Kerbelrip'.

Plants of the new variety can be compared to plants of the *Primula* cultivar 'Kerbelblic', U.S. Plant Pat. No. 32,385. Plants of the new *Primula* differed from plants of the cultivar 'Kerbelblic' in the following characteristics:

1. The comparator's flower color is purple; flower color of 'Kerbelrip' is white and blue-violet.

2. 'Kerbelrip' has an enlarged calyx; 'Kerbelblic' does not.

BRIEF DESCRIPTION OF THE PHOTOGRAPHS

The accompanying photograph in FIG. 1 illustrates in full color a typical plant of 'KERBELRIP' grown in Over, Cambridge, United Kingdom, in a glass-covered greenhouse. This plant was about 7 months old when the photographs were taken. During the production of the plants, day temperatures ranged from 5° to 15° C. and night temperatures ranged from 2° to 12° C.

Figure 2:
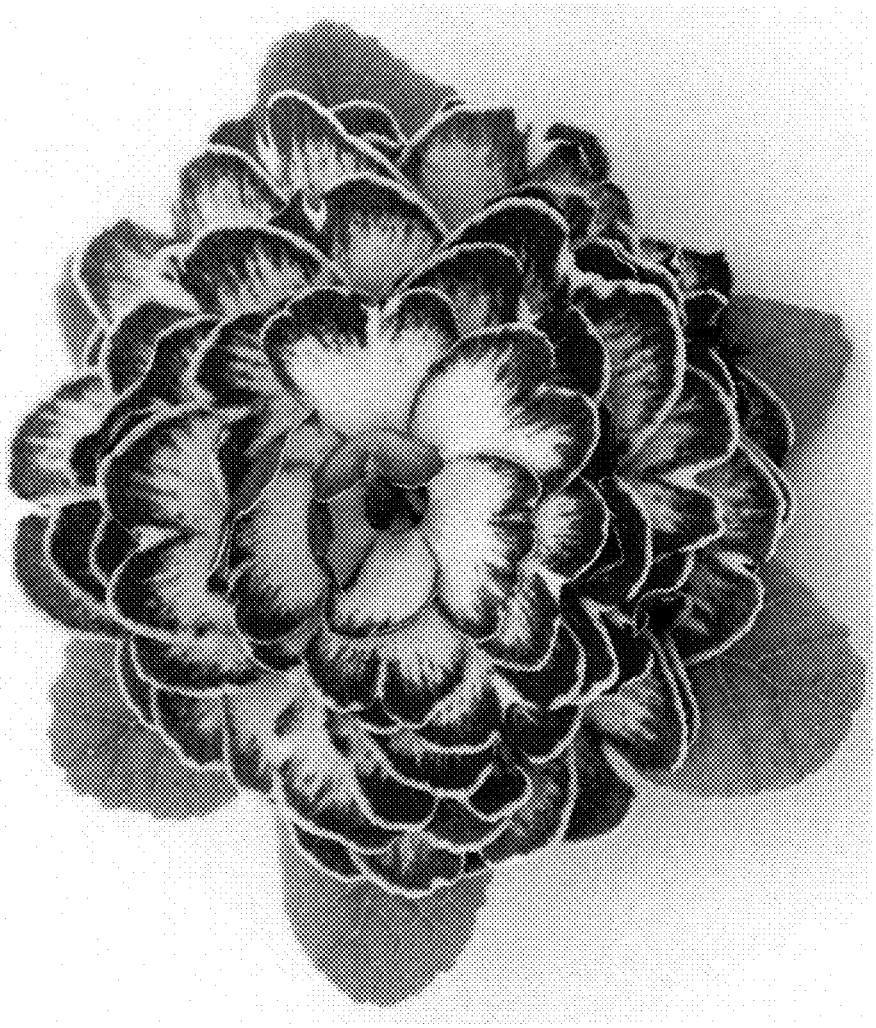

FIG. 2 illustrates a close up of a typical flower of 'KERBELRIP'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 except where general terms of ordinary dictionary significance are used. The following observations and measurements describe 'KERBELRIP' plants grown in a greenhouse in Cambridge, United Kingdom. During the production of the plants, day temperatures ranged from 1.5° C. to 25° C. and night temperatures ranged from 1.5° C. to 15° C. No chemical or photoperiodic treatments were given. Measurements were taken during Spring and numerical values represent averages of typical flowering types.

Botanical classification: *Primula vulgaris* 'KERBELRIP'.

Age of the plant described: Approximately 4 to 5 months in an 11 cm pot.

PROPAGATION

Method: Tissue culture.

Time to produce a rooted plant: About 6 weeks.

Root description: Fibrous, colored near RHS White 155A.

PLANT

Growth habit: Upright, compact and uniform.

Height: 31 cm.

Plant spread: 27 cm.

Branching characteristics: No branches, foliage emerges basally.

Vigor: Vigorous.

FOLIAGE

Leaf:

*Arrangement*.—Basal, simple.

*Length*.—13 cm.

*Width*.—5 cm.

*Shape*.—Oblanceolate.

*Apex*.—Obtuse.

*Base*.—Acute.

*Margin*.—Irregular, slightly crenulate and undulating.

*Texture of top surface*.—Rugose.

*Texture of bottom surface*.—Rugose with veins prominent.

*Color*.—Developing foliage upper side: RHS Yellow-Green 144A. Developing foliage under side: RHS Yellow-Green 146A and 146B. Mature foliage upper side: Near RHS Green NN137A. Mature foliage under side: Near RHS Green NN137B.

*Venation*.—Type: Pinnate. Venation color upper side: RHS Greyed-Green 195B and 195C. Venation color under side: RHS Greyed-Green 195B.

Petiole:

*Length*.—0.7 cm.

*Diameter*.—0.6 cm.

*Color*.—Upper Surface: RHS Yellow-Green 157A with Purple-Pink 186D overlaid near base. Lower Surface: RHS Yellow-Green 157A with Purple-Pink 186C overlaid near base.

*Texture upper surfaces*.—Glabrous.

*Texture lower surfaces*.—Pubescent.

*Strength*.—Strong.

FLOWER

Bloom period: Recurrent flowering during the Spring under United Kingdom outdoor conditions.

Flower type/habit: Solitary, rounded double flowers; flowers face upright and outward. Freely flowering.

Persistent or self-cleaning: Persistent.

Fragrance: None.

Flowers per inflorescence: 50 to 71 flowers and buds per plant. Each flower framed by an enlarged calyx.

Inflorescence size:

*Height*.—Average 10 cm.

*Diameter*.—Average 15 cm.

Flower bud:

*Height*.—1.75 cm.

*Diameter*.—1.25 cm.

*Shape*.—Conical.

*Texture*.—Glabrous.

*Color*.—RHS Violet 90A.

Individual flower:

*Diameter*.—6 cm.

*Depth*.—3 cm.

Petals:

*Quantity*.—45 to 55 per flower, in several concentric whorls.

*Length* (*including tube*).—3.4 cm.

*Width*.—1.8 cm.

*Shape*.—Obcordate.

*Apex*.—Emarginate.

*Margin*.—Entire, slightly undulating.

*Texture, upper and lower surfaces*.—Glabrous.

*Color*.—Developing petals, upper surface: Rim of RHS Violet 90A. Mid-section White NN155C. Base Yellow 13A (not visible on complete flower). Developing petals, lower surface: Rim of RHS Violet N88A fading towards mid-section. Small lower section of White NN155C. Base Yellow 13A. Mature petals, upper surface: Rim of RHS Violet N88A. Mid-section White NN155C. Base Yellow 13B (visible on central petals only). Mature petals, lower surface: Rim of RHS Violet 93B fading towards mid-section. Mid-section White 155A. Base Yellow 160D.

Sepals:

*Quantity*.—5 in a single whorl; fused at base. Sepals are large and frame the flower.

*Length*.—3.7 cm.

*Width*.—1.7 cm.

*Shape*.—Oblanceolate.

*Apex*.—Acute.
*Margin*.—Entire.
*Texture upper surfaces*.—Slightly rugose.
*Texture upper surfaces*.—Slightly rugose.
*Color, upper surface*.—Darker than RHS Yellow-Green 144A.
*Color, lower surface*.—RHS Yellow-Green 144A.

Peduncle:
*Length*.—9.5 cm.
*Diameter*.—0.2 cm.
*Orientation*.—Mostly erect.
*Strength*.—Strong.
*Color*.—RHS Orange N170D with a slight blush of Grey-Red 182B.
*Texture*.—Pubescent.

Pedicel:
*Length*.—2.5 cm.
*Diameter*.—0.2 cm.
*Orientation*.—Upwards and outwards.
*Strength*.—Strong.
*Color*.—RHS Yellow-Green 151D.
*Texture*.—Slightly pubescent.

REPRODUCTIVE ORGANS

Development of reproductive organs has not been observed.

OTHER CHARACTERISTICS

Disease resistance: Plants of the new *Primula* have not been noted to be resistant nor susceptible to pathogens and pests common to *Primula*.

Temperature tolerance: Plants of the new *Primula* have been observed to have tolerated temperatures from about −5° to 28° C.

Fruit/seed production: Fruit and seed production not observed; flowers are sterile.

What is claimed is:

1. A new and distinct cultivar of *Primula* plant named 'KERBELRIP' as herein illustrated and described.

* * * * *